United States Patent [19]

Scovill et al.

[11] Patent Number: 4,657,903
[45] Date of Patent: Apr. 14, 1987

[54] TRANSITION METAL COMPLEXES OF THE SELENIUM ANALOGS OF 2-ACETYL- AND 2-PROPIONYLPYRIDINE THIOSEMICARBAZONES USEFUL FOR TREATING MALARIAL INFECTIONS AND LEUKEMIA

[75] Inventors: John P. Scovill, Silver Spring; Daniel L. Klayman, Chevy Chase, both of Md.; Charles F. Franchino, Washington, D.C.

[73] Assignee: The United States of America as represented by the Secretary of the Army, Washington, D.C.

[21] Appl. No.: 364,089

[22] Filed: Mar. 31, 1982

[51] Int. Cl.$^4$ .................. A61K 31/44; C07F 15/00; C07F 1/08

[52] U.S. Cl. .................. 514/185; 514/186; 514/187; 514/188; 540/465; 540/541; 544/64; 544/225; 546/6

[58] Field of Search ............... 260/244.4, 550; 546/6, 546/331, 2; 544/64, 225; 424/245; 540/465, 541; 514/185, 186, 187, 188

[56] References Cited

U.S. PATENT DOCUMENTS

| | | | |
|---|---|---|---|
| 2,719,161 | 9/1955 | Behnisch et al. | 546/331 |
| 2,723,270 | 11/1955 | Scudi | 546/331 |
| 3,597,444 | 8/1971 | Klayman et al. | 260/550 |
| 3,824,282 | 7/1974 | Fry et al. | 260/550 |
| 4,317,776 | 3/1982 | Klayman et al. | 260/244.4 |

FOREIGN PATENT DOCUMENTS

| | | | |
|---|---|---|---|
| 0002625 | 5/1962 | Japan | 546/331 |
| 0002626 | 5/1962 | Japan | 546/331 |
| 1084700 | 9/1967 | United Kingdom | 546/331 |

OTHER PUBLICATIONS

Klayman et al., J. Am. Chem. Soc., vol. 95 (1), pp. 197–199 (1973).
Klayman et al., J. Med. Chem., vol. 22, (7), pp. 855–862 (1979).
Klayman et al., J. Med. Chem., vol. 22 (11), pp. 1367–1373 (1979).
Antholine et al., J. Med. Chem., vol. 19 (2), pp. 339–341 (1976).
Saryan et al., J. Med. Chem., vol. 22 (10), pp. 1218–1221 (1979).
French et al., J. Med. Chem., vol. 13 (6), pp. 1117–1124 (1970).

Primary Examiner—Donald G. Daus
Assistant Examiner—Diana G. Rivers
Attorney, Agent, or Firm—William G. Gapcynski; Arthur I. Spechler; Werten F. W. Bellamy

[57] ABSTRACT

This invention relates to novel transition metal complexes of 2-acetyl- and 2-propionylpyridine thiosemicarbazones, their selenium analogs. These compounds are useful as antimalarial and antileukemic agents. Also disclosed are several synthetic procedures used to prepare the thiosemicarbazones and their selenium analogs.

23 Claims, No Drawings

TRANSITION METAL COMPLEXES OF THE SELENIUM ANALOGS OF 2-ACETYL- AND 2-PROPIONYLPYRIDINE THIOSEMICARBAZONES USEFUL FOR TREATING MALARIAL INFECTIONS AND LEUKEMIA

GOVERNMENT INTEREST

The invention described herein may be manufactured, licensed and used by or for the Government, for governmental purposes, without the payment of any royalties to us thereon.

BACKGROUND OF THE INVENTION

Applicants reported in the *Journal of Medicinal Chemistry*, 1979, Vol. 22 at pages 855 and 1367 on a series of thiosemicarbazones derived from 2-acetylpyridine which possess significant antimalarial activity. The molecular features which have been shown to be essential for antimalarial activity are the presence of a 2-pyridylalkylidene moiety, an attached thiocarbonyl or selenocarbonyl group (in contrast to a carbonyl group) as reported in *Eur. J. Med. Chem.*, 1981, Vol. 16, page 317, and the presence of certain bulky substituents at position $N^4$. These are the same features which would be expected to produce effective transition metal chelating properties. The formation of metal complexes has been implicated in the mechanism of antitumor activity of the structurally related series of 2-formylpyridine thiosemicarbazones as described by F. A. French et al, *J. Med. Chem.*, 1970, Vol. 13, page 1117.

Saryan et al reported in *J. Med. Chem.*, 1979, Vol. 22, page 1218 that the iron complexes of some alpha-N-heterocyclic thiosemicarbazones are three to six-fold more active as inhibitors of ribonucleotide reductase than the free ligands. They also noted an enhancement of antitumor activity upon complexation. The antitumor properties of a number of transition metal complexes of methyl 3-[1-(2-pyridyl)-ethylidene]carbodithioate (I) have been reported by Das and Livingstone in *Br. J. Cancer*, 1978, Vol. 37, page 466. The chloro Ni(II) complex of compound I was the most active against P388 leukemia in mice, having a T/C of 153% at a dose of 6.2 mg/kg. The chloro Cu(II) complex was less active, having a T/C of 115% at a dose 0.8 mg/kg.

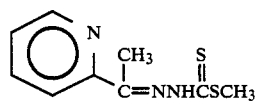

Compound I

In view of these considerations, applicants decided to prepare transition metal complexes of several selected 2-acetyl- and 2-propionylpyridine thiosemicarbazones and selenosemicarbazones in order to investigate their antimalarial and their antitumor properties.

DETAILED DESCRIPTION OF THE INVENTION

This invention relates to the use of the following compounds and their pharmaceutically-acceptable acid addition salts in the treatment of malaria and leukemia:

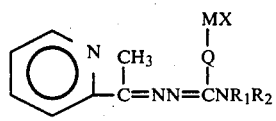

or a pharmaceutically-acceptable acid addition salt wherein Q represents sulfur or selenium; X represents a halogen atom such as chloride, or a thiocyanate group; M represents a transition metal such as Cu(II), Ni(II), Fe(III), or Mn(II); R is methyl or ethyl; $R_1$ is hydrogen, alkyl, preferably having 1 to 12 carbon atoms or more, preferably 6 to 12 carbon atoms; cycloalkyl, preferably having 3 to 10 carbon atoms; substituted alkyl wherein the alkyl group preferably has 1 to 12 carbon atoms and the substituent group is amine, alkylamino (preferably 1 to 4 carbon atoms), dialkylamino (preferably 1 to 4 carbon atoms in each alkyl group), cycloalkyl (preferably 3 to 10 carbon atoms), hydroxy, C(O)Oalkyl (preferably 1 to 4 carbon atoms in the alkyl group), phenyl, or pyridyl; alkenyl, preferably having 2 to 6 carbon atoms; alkynyl, preferably having 3 to 6 carbon atoms; substituted benzyl wherein the substituent is methyl or phenyl on the alpha carbon atom, or the substituent is alkyl (preferably methyl), dialkyl (preferably dimethyl), halo, dihalo, or alkoxy (preferably ethoxy) on the phenyl ring; adamantyl; phenyl; naphthyl; substituted phenyl or substituted naphthyl wherein the ring is mono-, di-, or trisubstituted and the substituents are alkyl (preferably 1 to 4 carbon atoms), halo (preferably fluoro), alkoxy (preferably 1 to 4 carbon atoms), hydroxy, phenoxy, trifluoromethyl, dialkyl (preferably dimethyl) amino, dialkylaminoalkyl (preferably diethylaminomethyl), or C(O)Oalkyl (preferably 1 to 4 carbon atoms in the alkyl group); pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:

(1) alkylenimino;

(2) alkylenimino which may contain one double bond and/or is mono- or disubstituted with alkyl (preferably 1 to 4 carbon atoms), hydroxy, phenyl, or benzyl;

(3) alkylenimino which is either bridged by an alkylene group (preferably 2 carbon atoms) or is fused to a phenyl ring; or is attached by a spiro linkage to an ethylene ketal group;

(4) homopiperazinyl; homopiperazinyl substituted with alkyl (preferably 1 to 4 carbon atoms); piperazinyl; or piperazinyl substituted with alkyl (preferably 1 to 4 carbon atoms), dialkyl (preferably 1 to 4 carbon atoms in each alkyl group), phenyl, C(O)Oalkyl (preferably 1 to 4 carbon atoms in the alkyl group), trifluoromethylphenyl, halophenyl, benzyl, or pyridyl; and (5) morpholino, dialkyl (preferably 1 to 4 carbon atoms in each alkyl group) morpholino.

When $R_1$ and $R_2$ are taken together with the nitrogen atom to which they are attached, the resulting heterocyclic ring is preferably one of the following: azetidino; pyrrolidino; 2,5-dimethylpyrrolidino; piperidino;

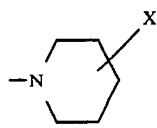

(wherein X is 2-methyl, 3-methyl, 4-methyl, 2-ethyl, 4-hydroxy, 4-phenyl, or 4-benzyl); hexamethylenimino; octamethylenimino; dodecamethylenimino; 2,6-dimethylpiperidino; 3,5-dimethyl piperidino; morpholino; 3,5-dimethylmorpholino;

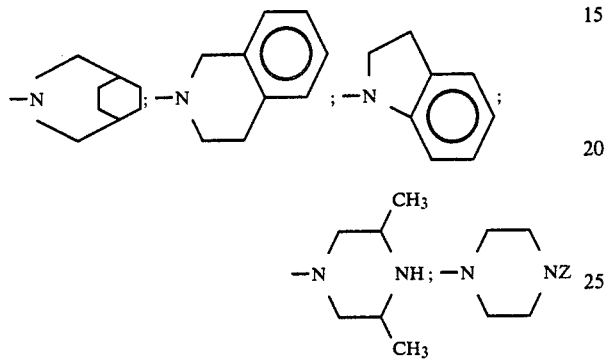

(wherein Z is methyl, phenyl, 3-trifluoromethylphenyl, benzyl, C(O)OEt, 3-pyridyl, 2-pyridyl, or 4-fluorophenyl);

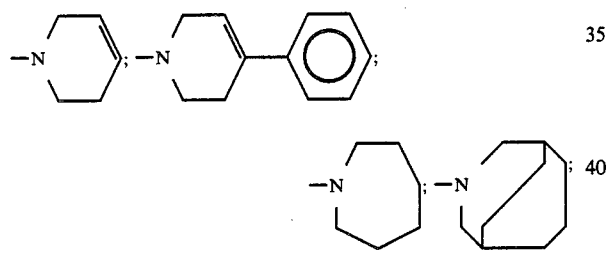

azacyclotridecyl;

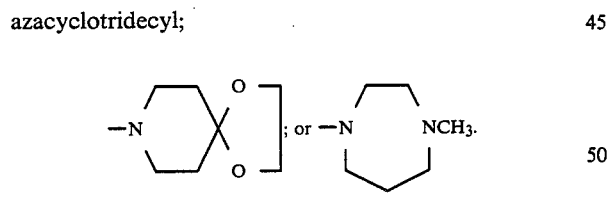

In this disclosure, it is understood that C(O)Oalkyl represents the alkyl carboxylic acid ester; for example, C(O)OEt represents the ethyl carboxylic acid ester.

A partial recitation of specific 2-alkylpyridine thiosemicarbazones and 2-alkylpyridine selenosemicarbazones contemplated within the scope of applicants' invention which form complexes with transition metals is depicted by the following formula:

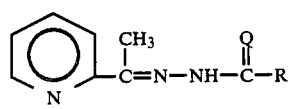

wherein R represents:

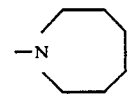    1.

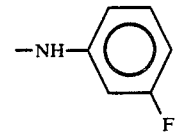    2.

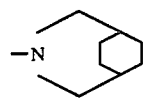    3.

—N—CH₂(CHOH)₄CH₂OH    4.
—N(CH₃)₂    5.

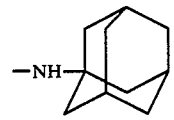    6.

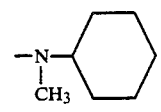    7.

—NHCH₃    8.
—NH₂    9.

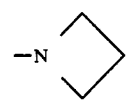    10.

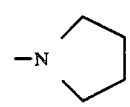    11.

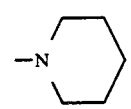    12.

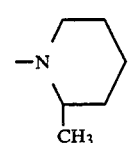    13.

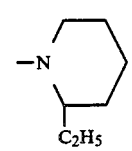    14.

    15.

—NH—CH₂—CH=CH₂    16.

-continued

17. 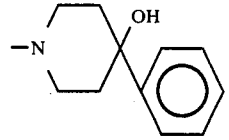

18. 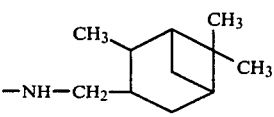

19.

20. 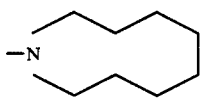

21. 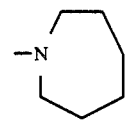

22. 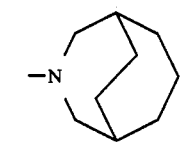

23.

24. 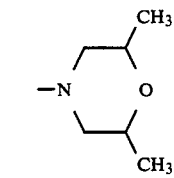

25. 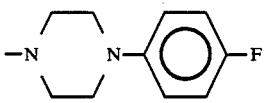

26. 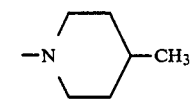

-continued

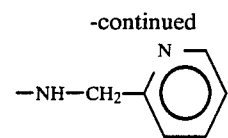 36.

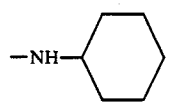 37.

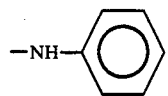 38.

—NHC(CH₃)₂CH₂C(CH₃)₃ 39.

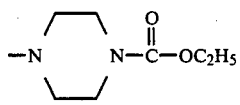 40.

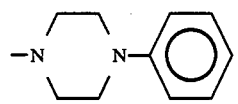 41.

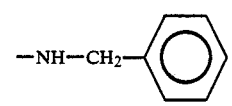 42.

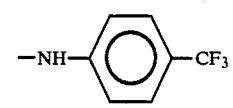 43.

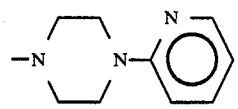

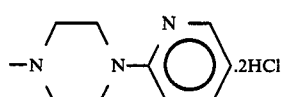

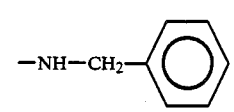

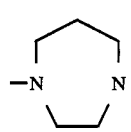

—NHCH₂C≡CH
—N(C₂H₅)₂
—NHCH₂CH₃
—NHC₄H₉
—NHC₈H₁₇
—NHC₁₀H₂₁

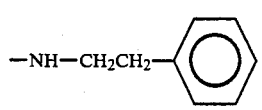

27. The chemical nomenclature for most of the 2-alkyl-pyridine thiosemicarbazones or selenosemicarbazones depicted in the preceeding paragraph are as follows:

1. 1-Azacycloheptane-1-thiocarboxylic acid 2-[1-(2-pyridyl)ethylidene]hydrazide and the 1-selenocarboxylic acid analog;

2. 2-Acetylpyridine 4-(3-fluorophenyl)-3-thiosemicarbazone and the 3-selenosemicarbazone analog;

3. 3-Azabicyclo[3.2.2]nonane-3-thiocarboxylic acid 2-[1-(2-pyridyl)ethylidene]hydrazide and the 3-selenocarboxylic acid analog;

4. 1-Methylamino-1-deoxy-D-glucitol-N-thiocarboxylic acid 2-[1-(2-pyridyl)ethylidene]hydrazide and the N-selenocarboxylic acid analog;

5. 2-Acetylpyridine 4,4-dimethylthiosemicarbazone and the 4,4-dimethylselenosemicarbazone analog;

6. 2-Acetylpyridine 4-(1-adamantyl)thiosemicarbazone and the 4-(1-adamantyl)selenosemicarbazone analog;

7. 2-Acetylpyridine 4-cyclohexyl-4-methylthiosemicarbazone and the 4-cyclohexyl-4-methylselenosemicarbazone analog;

8. 2-Acetylpyridine 4-methylthiosemicarbazone and the 4-methylselenosemicarbazone analog;

9. 2-Acetylpyridine thiosemicarbazone and the selenosemicarbazone analog;

10. Azetidine-1-thiocarboxylic acid 2-[1-(2-pyridyl)ethylidene]hydrazide and the 1-selenocarboxylic acid analog;

11. 1-Azacyclopentane-1-thiocarboxylic acid 2-[1-(2-pyridyl)ethylidene]hydrazide and the 1-selenocarboxylic acid analog;

12. Piperidine-1-thiocarboxylic acid 2-[1-(2-pyridyl)ethylidene]hydrazide and the 1-selenocarboxylic acid analog;

13. 2-Methylpiperidine-1-thiocarboxylic acid 2-[1-(2-pyridyl)ethylidene]hydrazide and the 1-selenocarboxylic acid analog;

14. 2-Ethylpiperidine-1-thiocarboxylic acid 2-[1-(2-pyridyl)ethylidene]hydrazide and the 1-selenocarboxylic acid analog;

15. 1-Azacyclotridecane-1-thiocarboxylic acid 2-[1-(2-pyridyl)ethylidene]hydrazide and the 1-selenocarboxylic acid analog;

16. 2-Acetylpyridine 4-allyl-3-thiosemicarbazone and the 3-selenosemicarbazone analog;

17. 2-Acetylpyridine 4-(2-picolyl)-3-thiosemicarbazone and the 3-selenosemicarbazone analog;

18. 2-Acetylpyridine 4-cyclohexyl-3-thiosemicarbazone and the 3-selenosemicarbazone analog;

19. 2-Acetylpyridine 4-phenyl-3-thiosemicarbazone and the 3-selenosemicarbazone analog;

20. 2-Acetylpyridine 4-(1,1,3,3-tetramethylbutyl)-3-thiosemicarbazone and the 3-selenosemicarbazone analog;

21. 1,4-Diaza-4-carboethoxycyclohexane-1-thiocarboxylic acid 2-[1-(2-pyridyl)ethylidene]hydrazide and the 1-selenocarboxylic acid analog;

22. 1,4-Diaza-4-phenylcyclohexane-1-thiocarboxylic acid 2[1-(2-pyridyl)ethylidene]hydrazide and the 1-selenocarboxylic acid analog;

23. 2-Acetylpyridine 4-(2-methylbenzyl)-3-thiosemicarbazone and the 3-selenosemicarbazone analog;

24. 2-Acetylpyridine 4-(4-trifluoromethylphenyl)-3-thiosemicarbazone and the 3-selenosemicarbazone analog;

25. 1,4-Diaza-4-(2-pyridyl)cyclohexane-1-thiocarboxylic acid 2[1-(2-pyridyl)ethylidene]hydrazide and the 1-selenocarboxylic acid analog;

26. 1,4-Diaza-4-(2-pyridyl)cyclohexane-1-thiocarboxylic acid 2-[1-(2-pyridyl)ethylidene]hydrazide dihydrochloride and the 1-selenocarboxylic acid analog;

27. 2-Acetylpyridine 4-benzyl-3-thiosemicarbazone and the 3-selenosemicarbazone analog;

28. 1,4-Diaza-4-methylcycloheptane-1-thiocarboxylic acid 2-[1-(2-pyridyl)ethylidene]hydrazide and the 1-selenocarboxylic acid analog;

29. 2-Acetylpyridine 4-(2-propynyl)-3-thiosemicarbazone and the 3-selenosemicarbazone analog;

30. 2-Acetylpyridine 4,4-diethylthiosemicarbazone and the 4,4-diethylselenosemicarbazone analog;

31. 2-Acetylpyridine 4-ethylthiosemicarbazone and the 4-ethylselenosemicarbazone analog;

32. 2-Acetylpyridine 4-butylthiosemicarbazone and the 4-butylselenosemicarbazone analog;

33. 2-Acetylpyridine 4-octylthiosemicarbazone and the 4-octylselenosemicarbazone analog;

34. 2-Acetylpyridine 4-decylthiosemicarbazone and the 4-decylselenosemicarbazone analog;

35. 2-Acetylpyridine 4-(2-phenethyl)thiosemicarbazone and the 4-(2-phenethyl)selenosemicarbazone analog;

36. (4-Hydroxy-4-phenylpiperidine)-1-thiocarboxylic acid 2-[1-(2-pyridyl)ethylidene]hydrazide and the 1-selenocarboxylic acid analog;

37. 2-Acetylpyridine 4-(3-pinylmethyl)thiosemicarbazone and the 4-(3-pinylmethyl)selenosemicarbazone; and 38. 1-Azacyclononane-1-thiocarboxylic acid 2-[1-(2-pyridyl)ethylidene]hydrazide and the 1-selenocarboxylic acid analog.

The above-described compounds and their pharmaceutically-acceptable acid addition salts are useful in the treatment of malarial infections and leukemia.

With respect to the pharmaceutically-acceptable acid addition salts of this invention, it will be apparent to those of ordinary skill in the art that such salts are contemplated only where the structural features of the compounds permit their preparation. As non-limiting examples of acids used to prepare such salts, hydrochloric and hydrobromic acids are representative.

SYNTHETIC PROCEDURES

Preparation of Thiosemicarbazones

Three synthetic procedures proved to be useful for preparing the thiosemicarbazones of this invention. In Scheme A, a primary amine was converted to the corresponding isothiocyanate (1), ordinarily by employing thiophosgene. Reaction of 1 with hydrazine afforded a thiosemicarbazide 2. Condensation of this intermediate with 2-acetylpyridine provided the 4-monosubstituted thiosemicarbazone 3. However, only thiosemicarbazones monosubstituted at position 4 can be prepared in this manner,

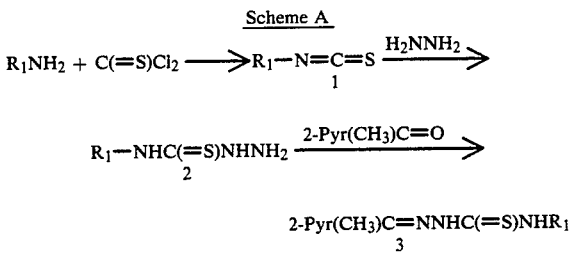

as 2-acetylpyridine proved to be usually resistant to condensation with 2,4-disubstituted thiosemicarbazides.

In Scheme B, reaction of hydrazine and carbon disulfide in the presence of sodium hydroxide yielded a carbodithioate. Alkylation of this carbodithioate with either iodomethane or dimethyl sulfate gave methyl hydrazinecarbodithioate (4). Condensation of 4 with 2-acetylpyridine gave the versatile intermediate, methyl 3-[1-(2-pyridyl)ethylidene]hydrazinecarbodithioate, 5. Reaction of 5 with primary amines gave 4-monosubstituted thiosemicarbazones such as 3 while secondary amines or cyclic amines produced 4,4-disubstituted thiosemicarbazones, 6. In addition, reaction of 5 was not limited to more active nucleophiles, as excellent yields could be obtained with many primary aromatic amines. However, 5 was resistant to reaction with some secondary aromatic amines, such as N-methylaniline.

Scheme B

H$_2$NNHC(=S)SCH$_3$ + 2-Pyr(CH$_3$)C=O ⟶
4

2-Pyr(CH$_3$)C=NNHC(=S)SCH$_3$ $\xrightarrow{HNR_1R_2}$
5

2-Pyr(CH$_3$)C=NNHC(=S)NR$_1$R$_2$
6

Scheme C involved the reaction of 2-acetylpyridine with hydrazine to yield the hydrazone 7. Reaction of this hydrazone with an isothiocyanate 1 produced a 4-monosubstituted thiosemicarbazone 3. This reaction was especially useful when the required isothiocyanate was commercially available.

Scheme C

2-Pyr(CH$_3$)C=O + H$_2$NNH$_2$ ⟶

2-Pyr(CH$_3$)C=NNH$_2$ $\xrightarrow{1}$ 3
7

Preparation of Selenosemicarbazones

The synthetic procedures useful for preparing the selenosemicarbazones of this invention are as follows:

Scheme D

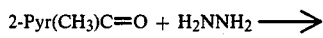

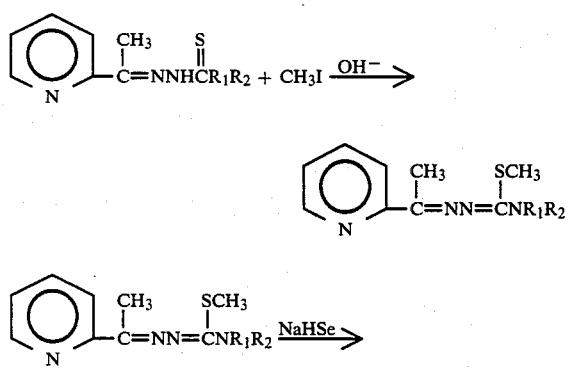

-continued
Scheme D

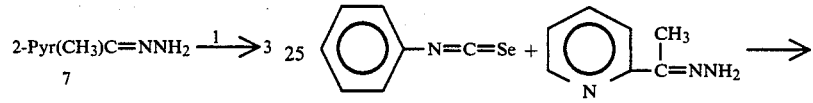

In Scheme D, S-methylation of the thiosemicarbazones was performed in the presence of aqueous or alcoholic base. The resulting products were allowed to react with sodium hydrogen selenide under an inert atmosphere.

Scheme E

Se° + NaBH$_4$ ⟶ NaHSe ⟶ Na$_2$Se

Na$_2$Se + 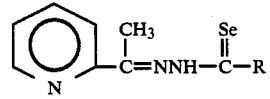

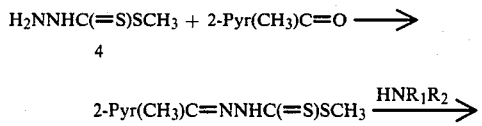

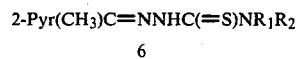

Scheme E represents an alternative method for making the N$^4$-phenyl derivative by a reaction of phenylisoselenocyanate with 2-acetylpyridine hydrazone. The compound obtained, 2-acetylpyridine 4-phenyl-3-selenosemicarbazone, was identical to that made by the displacement reaction described in Scheme D. The phenylisoselenocyanate reactant was prepared by a simplified procedure from phenylisocyanide dichloride and sodiumselenide. The latter was generated from elemental selenium and sodium borohydride in ethanol giving sodium hydrogen selenide which was then combined with one equivalent of sodium hydroxide as described by Daniel L. Klayman et al in *J. Amer. Chem. Soc.*, 1973, Vol. 95, page 197.

The following Table 1 further illustrates and provides descriptive information concerning certain 2-acetylpyridine 3-selenosemicarbazones prepared in accordance with Scheme D.

TABLE 1

2-Acetylpyridine 3-Selenosemicarbazones

| Compound No. | R | Mp. °C. | Formula | Yield,[a] % | Recryst. solvent |
|---|---|---|---|---|---|
| 1 | -N⟨piperazinyl⟩N-⟨2-pyridyl⟩ | 182–184 dec | C$_{17}$H$_{20}$N$_6$Se | 49 | CH$_3$CN |

TABLE 1-continued

2-Acetylpyridine 3-Selenosemicarbazones

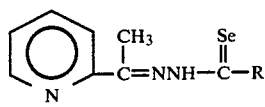

| Compound No. | R | Mp. °C. | Formula | Yield,[a] % | Recryst. solvent |
|---|---|---|---|---|---|
| 2 | -N(CH(CH₃)CH₂)₂O (2,6-dimethylmorpholino) | 179–180 dec | $C_{14}N_{20}N_4OSe$ | 34 | $CH_3OH$ |
| 3 | -NH-C₆H₅ | 152–154 dec | $C_{14}N_{14}N_4Se$ | 36 | EtOH |
| 4 | -N(cycloheptyl, as azacycle) | 160–161 | $C_{16}H_{22}N_4Se$ | 49 | $CH_3OH$ |
| 5 | -N(piperazinyl)-C₆H₄-F | 198–200 dec | $C_{18}H_{20}FN_5Se$ | 36 | $CH_3OH$ |
| 6 | -N(hexamethyleneimino) | 170–171 dec | $C_{14}H_{20}N_4Se$ | 45 | EtOH |
| 7 | -N(azetidinyl) | 175–176 dec | $C_{11}N_{14}N_4Se$ | 38 | EtOH |
| 8 | -N(2-methylpiperidino) | 135–136 | $C_{14}H_{20}N_4Se$ | 22 | EtOH |
| 9 | -N(4-methylpiperidino) | 146–147 dec | $C_{14}H_{20}N_4Se$ | 52 | $CH_3OH$ |
| 10 | -N(CH₃)₂ | 172–175 dec | $C_{10}H_{14}N_4Se$ | 58 | $CH_3CN$ |
| 11 | -N(CH₂CH₃)₂ | 135–136 | $C_{12}N_{18}N_4Se$ | 39 | EtOH |

[a]Yields have not been optimized.

Preparation of Transition Metal Complexes of Thiosemicarbazones and Selenosemicarbazones The preparation of the requisite thiosemicarbazones and selenosemicarbazones has been described in Schemes A through E. In solution, thiosemicarbazones probably form an equilibrium mixture of the thione (IIa) and thiol (IIb) tautomers. Loss of the thiol proton from the form IIb affords a

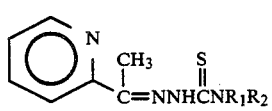

IIa

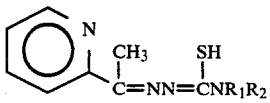
IIb singly charged tridentate ligand. The illustrative ligands designated below as IIIa, IIIb, IV, V, have high affinities for first row transition metal ions as evidenced by immediate and nearly quantitative formation of complexes when solutions of metal salts and thiosemicarbazones are combined.

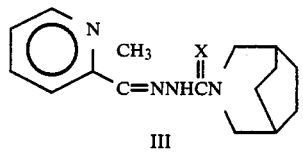

III

IIIa, X = S
IIIb, X = Se

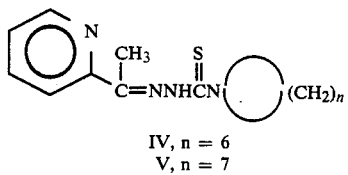

IV, n = 6
V, n = 7

By combining equimolar warmed ethanolic solutions of the thio- or selenosemicarbazones and the transition metal chloride, the chloro complex separated from the hot solution. Thiocyanato complexes of Ni(II) and Cu(II) were formed by refluxing a solution of the thiosemicarbazone with $(NH_4)_2Ni(SCN)_4$ or $Cu(SCN)_2(NH_3)_4$, respectively. In addition, the chloro complex compound referred to in Table 2 as complex compound 7 could be converted to thiocyanato complex compound 11 by refluxing a propionitrile solution of complex compound 7 and potassium thiocyanate.

The products which were obtained from Cu(II), Fe(III), and Ni(II) are mono ligand complexes whose structures (VI) are represented below.

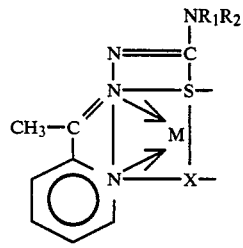
VI

However, the product obtained by reaction of $MnCl_2$ with thiosemicarbazone IV above was unusual in that it is the only di-ligand complex encountered by applicants. Details of stereochemistry, coordination number, and electronic structure are not known.

The ligands of the complex compounds referred to in Table 2 as IV, IIIa, IIIb and V are as defined in the previous section herein entitled "Preparation of Transition Metal Complexes of Thiosemicarbazones and Selenosemicarbazones".

EXAMPLES

The working examples set forth below illustrate, without any implied limitation, the preparation of representative compounds and salts useful in the practice of this invention in the treatment of malaria and leukemia.

Example 1

2-Acetylpyridine 4-allyl-3-thiosemicarbazone (Procedure C)

A solution of 2.7 g (0.02 mole) of 2-acetylpyridine hydrazone in 5 ml of MeOH was treated with 3.1 g (0.03 mol) of allyl isothiocyanate and the solution was heated at reflux for 3 hours. The solution was cooled and the product which formed was collected. The crude material was recrystallized 3 times from MeOH, affording 2.5 g (49%) of white needles of 2-acetylpyridine 4-allyl-3-thiosemicarbazone, mp 107° C.

Analysis Calcd. for $C_{11}H_{14}N_4S$: C, 56.38; H, 6.02; N, 23.91; S, 13.68. Found: C, 56.09; H, 6.11; N, 24.36; S, 13.89.

Example 2

2-Acetylpyridine 4-cyclohexyl-3-thiosemicarbazone (Procedure C)

A solution of 6.76 g (0.05 mol) of 2-acetylpyridine hydrazone in 10 ml of MeOH was treated with 7.2 g (0.05 mol) of cyclohexyl isothiocyanate and the solution was heated at reflux for 3 hours. The solution was chilled, and the crystals which formed were collected. Recrystallization of the product from 150 ml of MeOH afforded 6.40 g (46%) of white needles of 2-acetylpyridine 4-cyclohexyl-3-thiosemicarbazone, mp 155° C.

Analysis Calcd. for $C_{14}H_{20}N_4S$: C, 60.84; H, 7.29; N, 20.27; S, 11.60. Found: C, 60.76; H, 7.19; N, 20.16; S, 11.73.

Example 3

2-Acetylpyridine 4-(2-diethylaminoethyl)-3-thiosemicarbazone dihydrobromide (Procedure A)

By the application of the procedure of R. S. McElhinney [J. Chem. Soc. (c), 950 (1966)], 2-diethylaminoethylisothiocyanate, (bp 54°–55° C./1.5 mm Hg), was prepared in 20% yield.

Analysis Calcd. for $C_7H_{14}N_2S$: C, 53.12; H, 8.92; N, 17.70; S, 20.26. Found: C, 52.97; H, 8.76; N, 18.01; S, 20.47.

A solution of 1 g (0.063 mol) of 2-diethylaminoethylisothiocyanate in 5 ml of MeCN was treated with 0.3 g (0.063 mol) of 85% hydrazine hydrate. The solution was heated at reflux for 10 minutes and the solvent was removed under reduced pressure. The residue was then recrystallized from $C_6H_6$ affording 750 mg (63%) of white needles of 4-(2-diethylaminoethyl)-3-thiosemicarbazide, mp 83°–83.5° C.

Analysis Calcd. for $C_7H_{18}N_4S$: C, 44.18; H, 9.53; N, 29.44; S, 16.85. Found: C, 44.19; H, 9.46; N, 29.56; S, 16.60.

A solution of 605 mg (5 mmol) of 2-acetylpyridine in 10 ml of MeCN was treated with 950 mg (5 mmol) of 4-(2-diethylaminoethyl)-3-thiosemicarbazide and the solution was heated at reflux for 10 hours. The pH of the solution was adjusted to 6 with concentrated HBr and diluted with 15 ml of Et$_2$O. An oil which separated from solution soon solidified. Crystallization of this product from MeOH-MeCN afforded 1.42 g (64%) of yellow crystals of 2-acetylpyridine 4-(2-diethylaminoethyl)-3-thiosemicarbazone dihydrobromide, mp 231° C.

Analysis Calcd. for C$_{14}$H$_{23}$N$_5$S 2HBr: C, 36.93; H, 5.54; N, 15.38; S, 7.04. Found: C, 36.99; H, 5.52; N, 15.30; S, 7.07.

Example 4

2-Acetylpyridine 4-(3-fluorophenyl)-3-thiosemicarbazone (Procedure A)

2-Acetylpyridine (2.0 g, 0.0165 mol) in 70 ml of EtOH and 2.78 g (0.015 mol) 4-(3-fluorophenyl)-3-thiosemicarbazide (mp 152°–155° C.) were heated at reflux temperature for 4 hours. The solution was refrigerated overnight and the product was collected. Recrystallization from MeCN afforded 1.1 g (25%) of 2-acetylpyridine 4-(3-fluorophenyl)-3-thiosemicarbazone, mp 159°–160° C.

Analysis Calcd. for C$_{14}$H$_{13}$FN$_4$S: C, 58.32; H, 4.54; N, 19.43; S, 11.12. Found: C, 57.87; H, 4.70; N, 19.41; S, 11.08.

Example 5

2-Acetylpyridine 4,4-diisobutyl-3-thiosemicarbazone (Procedure B)

A solution of 10 g (0.044 mol) of methyl 3-[1-(2-pyridyl)ethylidene]hydrazinecarbodithioate in 25 ml of MeOH was treated with 7.5 g (0.058 mol) of diisobutylamine and heated at reflux for 6 hours. The solution was chilled and the crystals which formed were collected. Recrystallization from 130 ml of heptane afforded 8.6 g (64%) of yellow needles of 2-acetylpyridine 4,4-diisobutyl-3-thiosemicarbazone, mp 96° C.

Analysis Calcd. for C$_{16}$H$_{26}$N$_4$S: C, 62.71; H, 8.55; N, 18.28; S, 10.46. Found: C, 63.27; H, 8.50; N, 18.14; S, 10.21.

Example 6

Azacycloheptane-1-thiocarboxylic acid 2-[1-(2-pyridyl)ethylidene]hydrazide (Procedure B)

A solution of 5.0 g (0.022 mol) of methyl 3-[1-(2-pyridyl)ethylidene]hydrazinecarbodithioate in 15 ml of MeOH was treated with 2.2 g (0.022 mol) of hexamethylenimine and heated at reflux for 5 hours. The solution was chilled, scratched and the product which separated was collected. Recrystallization from 150 ml of MeOH afforded 3.4 g (56%) of yellow needles of azacycloheptane-1-thiocarboxylic acid 2-[1-(2-pyridyl)ethylidene]hydrazide, mp 165° C.

Analysis Calcd. for C$_{14}$H$_{20}$N$_4$S: C, 60.84; H, 7.29; N, 20.27; S, 11.60. Found: C, 60.91; H, 7.20; N, 20.30; S, 11.89.

Example 7

3-Azabicyclo[3.2.2]heptane-3-thiocarboxylic acid 2-[1-(2-pyridyl)ethylidene]hydrazide (Procedure B)

A solution of 3.8 g (0.018 mol) of methyl 3-[1-(2-pyridyl)ethylidene]hydrazinecarbodithioate and 2.1 g (0.017 mol) of 3-azabicyclo[3.2.2]nonane was heated at reflux for 5 hours. The solution was cooled, and the product which crystallized was collected. Recrystallization from 160 ml of MeOH afforded 3.34 g (65%) of yellow needles of 3-azabicyclo[3.2.2]nonane-3-thiocarboxylic acid 2-[1-(2-pyridyl)ethylidene]hydrazide, mp 156° C.

Analysis Calcd. for C$_{16}$H$_{22}$N$_4$S: C, 63.54; H, 7.33; N, 18.53; S, 10.60. Found: C, 63.51; H, 7.25; N, 18.55; S, 10.67.

Example 8

2-Acetylpyridine 4-cyclohexyl-4-methyl-3-thiosemicarbazone (Procedure B)

A solution of 10 g (0.044 mol) of methyl 3-[1-(2-pyridyl)ethylidene]hydrazinecarbodithioate in 25 ml of MeOH was treated with 7.5 g (0.066 mol) of N-methylcyclohexylamine and the solution heated at reflux for 8 hours. The solution was cooled overnight and the product which crystallized was collected. Recrystallization from cyclohexane afforded 9.3 g (72%) of 2-acetylpyridine 4-cyclohexyl-4-methyl-3-thiosemicarbazone, mp 96° C.

Analysis Calcd. for C$_{15}$H$_{22}$N$_4$S: C, 62.03; H, 7.64; N, 19.29; S, 11.04. Found: C, 62.07; H, 7.74; N, 19.23; S, 11.14.

Example 9

2-Acetylpyridine 4-(2-methylbenzyl)-3-thiosemicarbazone (Procedure B)

Methyl 3-[1-(2-pyridyl)ethylidene]hydrazinecarbodithioate (4.51 g, 0.02 mol) and 3.64 g (0.03 mol) 2-methylbenzylamine in 25 ml of methanol were heated under reflux for 36 hours followed by overnight refrigeration. The solid material which separated from solution was collected by filtration and recrystallized 3 times from ethanol to afford 3.85 g (48%) of white crystalline 2-acetylpyridine 4-(2-methylbenzyl)-3-thiosemicarbazone having a melting point of 152°–154° C.

Analysis Calcd. for C$_{16}$H$_{18}$N$_4$S: C, 64.40; H, 6.08; N, 18.78; S, 10.74. Found: C, 64.17; H, 6.23; N, 19.14; S, 10.64.

Example 10

4-(2-Pyridyl)-1-piperazinethiocarboxylic acid 2-[1-(2-pyridyl)ethylidene]hydrazide (Procedure B)

Methyl 3-[1-(2-pyridyl)ethylidene]hydrazinecarbodithioate (3.60 g, 0.016 mol) in 40 ml of EtOH was combined with 3.60 g (0.02 mol) of 1-(2-pyridyl)piperazine. The solution was heated at reflux for 18 hours, cooled and the yellow product which separated was collected. Recrystallization from MeCN afforded 3.45 g (60%) of 4-(2-pyridyl-1-piperazinethiocarboxylic acid 2-[1-(2-pyridyl)ethylidene]hydrazide, mp 187°–188° C.

Analysis Calcd. for C$_{17}$H$_{20}$N$_6$S: C, 59.98; H, 5.92; N, 24.69; S, 9.42. Found: C, 60.65; H, 5.90; N, 24.61; S, 9.41.

Example 11

2-Acetylpyridine 4-(2-pyridyl)-3-thiosemicarbazone (Procedure A)

4-(2-Pyridyl)-3-thiosemicarbazide (1.68 g, 0.01 mol) in 125 ml of EtOH and 7.5 ml of glacial acetic acid was treated with 1.21 g (0.01 mol) of 2-acetylpyridine. The solution was heated at reflux for 3 hours, cooled and the product collected. Recrystallization from MeCN afforded 1.8 g (66%) of 2-acetylpyridine 4-(2-pyridyl)-3-thiosemicarbazone, mp 185°–187° C.

Analysis Calcd. for $C_{13}H_{13}N_5S$: C, 57.54; H, 4.83; N, 25.81; S, 11.82. Found: C, 57.03; H, 5.08; N, 25.96; S, 12.17.

Example 12

2-Acetylpyridine 4-(1-adamantyl)-3-thiosemicarbazone (Procedure A)

A solution of 1.5 g (0.03 mol) of hydrazine hydrate in 50 ml of EtOH was treated with 3.86 g (0.02 mol) of 1-adamantyl isothiocyanate, and stirred for one hour at room temperature. The product was collected and washed two times with EtOH, affording 4.33 g (96%) of 4-(1-adamantyl)-3-thiosemicarbazide, mp 206°–207° C. This thiosemicarbazide is disclosed in *Chemical Abstracts*, 70: 11223 (1969); and in U.S. Pat. No. 3,406,180.

2-Acetylpyridine (2.65 g, 0.022 mol) in 50 mol of EtOH and 2 ml of glacial acetic acid was combined with 4.33 g (0.0195 mol) of 4-(1-adamantyl)-3-thiosemicarbazide, and the solution was heated at reflux for 24 hours. The solution was cooled and the product was collected. Recrystallization from MeCN afforded 3.63 g (50%) of 2-acetylpyridine 4-(1-adamantyl)-3-thiosemicarbazone, mp 172°–173° C.

Analysis Calcd. for $C_{18}H_{24}N_4S$: C, 65.82; H, 7.36; N, 17.06; S, 9.76. Found: C, 66.04; H, 7.22; N, 16.88; S, 9.71.

Example 13

2-Acetylpyridine 4,4-dimethyl-3-thiosemicarbazone (Procedure A)

To a solution of 2.39 g (0.02 mol) of 4,4-dimethyl-3-thiosemicarbazide in 75 ml of EtOH was added 2.54 g (0.021 mol) of 2-acetylpyridine. After heating at reflux for eight hours, the solution was cooled and the product was collected. Recrystallization from MeOH afforded 1.2 g (26%) of 2-acetylpyridine 4,4-dimethyl-3-thiosemicarbazone, mp 149°–150° C.

Analysis Calcd. for $C_{10}H_{14}N_4S$: C, 54.03; H, 6.35; N, 25.20; S, 14.42. Found: C, 53.83; H, 6.74; N, 25.25; S, 14.72.

Example 14

2-Acetylpyridine 4,4-dimethyl-3-thiosemicarbazone (Procedure B)

Methyl 3-[1-(2-pyridyl)ethylidene]hydrazinecarbodithioate (9.02 g, 0.04 mol) in 30 ml of EtOH was combined with 5.2 g (0.08 mol) of dimethylamine (40% aqueous solution). The resulting solution was heated at reflux for 24 hours and the excess dimethylamine was removed under water-pump aspiration for 15 minutes. The solution was filtered and cooled to give 7.3 g (82%) of bright yellow crystals of 2-acetylpyridine 4,4-dimethyl-3-thiosemicarbazone, mp 155°–156° C. whose infrared spectrum was identical to that of the product made by the method described in Example 13.

Example 15

1-Azacycloheptane-1-thiocarboxylic acid 2-[1-(2-pyridyl)propylidene]hydrazide (Procedure B)

Methyl 3-[1-(2-pyridyl)propylidene]hydrazinecarbodithioate (4.77 g, 0.02 mol) and 3.4 ml (3.0 g, 0.03 mol) hexamethylenimine in 25 ml of MeOH were heated under reflux for 48 hours followed by overnight refrigeration. The solid material which separated from solution was collected by filtration and recrystallized from MeOH to afford 3.65 g (63%) of yellow crystalline 1-azacycloheptane-1-thiocarboxylic acid 2-[1-(2-pyridyl)propylidene]hydrazide, mp 117°–119° C.

Analysis Calcd. for $C_{15}N_{22}N_4S$: C, 62.03; H, 7.64; N, 19.29; S, 11.04. Found: C, 62.15; H, 7.64; N, 19.14; S, 11.16.

The compounds listed in Table 1 as 1–11 were prepared by the method exemplified in the following description of the preparation of 2-acetylpyridine 4,4-dimethyl-3-selenosemicarbazone.

Example 16

2-Acetylpyridine 4,4-dimethyl-3-selenosemicarbazone (Procedure D)

A suspension of 3.0 g (13.5 mmol) of 2-acetylpyridine 4,4-dimethyl-3-thiosemicarbazone in 10 ml of $H_2O$ was treated with 5 ml of 50% w/w solution of aqueous NaOH. The suspension was stirred for 5 minutes, and then 2.28 g (16.1 mmol) of iodomethane was added dropwise to the rapidly stirred mixture, converting the yellow solid into a yellow oil. The oil was extracted into 50 ml of $Et_2O$ ($3 \times 50$ ml) and brine ($1 \times 50$ ml) and dried ($MgSO_4$). The solvent was removed under reduced pressure and the resulting S-methyl compound of the formula 2-acetylpridine 4,4-dimethyl-3-methylthiosemicarbazone, as an oil, was used without further purification for the succeeding step.

A solution of sodium hydrogen selenide was prepared by combining 1.18 g (15 mmol) of Se with 0.64 g (17 mmol) of sodium borohydride in 25 ml of EtOH under argon. A solution of the S-methyl compound in 25 ml of EtOH was added in a single portion, the reaction mixture was stirred for 40 hours, and poured into 50 ml of 10% aqueous acetic acid. The product was extracted into 50 ml of $CHCl_3$ which was then washed with $H_2O$ ($3 \times 50$ ml), dried over $MgSO_4$, and the solvent was removed under reduced pressure. Crystallization of the selenosemicarbazone from MeCN afforded orane needles. IR: 1615, 1577, 1513, 1494, 1430, 1401, 1382, 1360, 1340, 1296, 1252, 1235, 1157, 977, 778 $cm^{-1}$.

Example 17

N-Phenyl-2-[-1-(2-pyridinyl)ethylidene]hydrazinecarboselenoamide (Procedure E)

Absolute ethanol (25 ml) was added with mechanical stirring and ice bath cooling to 3.5 g (45 mmol) of selenium and 1.9 g (50 mmol) of sodium borohydride under an inert atmosphere. The ice bath was removed after initial foaming subsided. The solution was allowed to stir for 20 minutes, was treated with 1.8 g (45 mmol) of NaOH dissolved in 5 ml of water, to which was added 6.53 g (37.5 mmol) of phenylisocyanide dichloride causing the immediate appearance of an opaque orange color. After an additional 4 hours of stirring, the mixture was treated with 120 ml of H$_2$O and extracted with 3×30 ml of Et$_2$O. The yellow extracts were combined, dried over CaCl$_2$, and the Et$_2$O was removed under reduced pressure. The opaque product was redissolved in 20 ml of petroleum ether, filtered, and the solvent was removed yielding 3.6 g (52%) of phenylisoselenocyanate as a pungent red oil which was used without further purification. IR: 2110 (N=C=Se), 2050, 1590, 1480, 850, 755 cm$^{-1}$.

To a solution of 2.6 g (20 mmol) of 2-acetylpyridine hydrazone in 25 ml of CH$_3$CN was added 3.6 g (20 mmol) of phenylisoselenocyanate. The clear red solution was heated with stirring to 45° C. for 3 hours, the solution was cooled to room temperature, and the crystals which separated were collected. Recrystallization of the product from EtOH gave 2.83 g (45%) of N-phenyl-2-[1-(2-pyridinyl)ethylidene]hydrazinecarboselenoamide as fine yellow needles, mp 153°–156° C.

Example 18

Chloro[3-azabicyclo[3.2.2]nonane-3-thiocarboxylic acid 2-[1-(2-pyridyl)ethylidene]hydrazonato]copper(II)-complex compound 7 of Table 2. The method for the preparation of the metal complexes of 2-acetylpyridine thiosemicarbazones is exemplified in the following procedure. A solution of 8.20 g (27 mmol) of 3-azabicyclo[3.2.2]nonane-3-thiocarboxylic acid 2-[1-(2-pyridyl)ethylidene]hydrazide in 400 ml of hot EtOH was treated with a solution of 4.60 g (27 mmol) of CuCl$_2$·2H$_2$O in 50 ml of hot EtOH. The product which separated was collected, washed with EtOH, and dried. An analytical sample was prepared by two recrystallizations from N,N-dimethylformamide. IR: 2935, 2863, 1595, 1492, 1467, 1445, 1435, 1295, 1205, 874, 767, 330 cm$^{-1}$.

Example 19

Thiocyanato[3-azabicyclo[3.3.2]nonane-3-thiocarboxylic acid 2-[1-(2-pyridyl)ethylidene]hydrazinato]copper(II)-complex compound 11 of Table 2.

Method A.

A solution of 200 mg (0.66 mmol) of 3-azabicyclo[3.2.2]nonane-3-thiocarboxylic acid 2-[1-(2-pyridyl)ethyldene]hydrazide in 10 ml of EtOH was treated with a solution of 164 mg (0.66 mmol) of Cu(SCN)$_2$4(NH$_3$) in ethanolic ammonium hydroxide (5 ml of EtOH+2 ml of concentrated NH$_4$OH). The solution was heated to boiling, filtered, and chilled. The crystals which separated were collected and washed with MeOH. An analytical sample was prepared by recrystallization from MeCN. IR: 2940, 2910, 2870, 2084 (SCN$^-$), 1601, 1495, 1460, 1437, 1300, 1274, 1202, 877, 778, 771 cm$^{-1}$.

Method B.

A solution of 500 mg (1.25 mmol) of complex compound 7 of Table 2 in 75 ml of refluxing propionitrile was treated with a solution of 122 mg (1.25 mmol) of KSCN in 20 ml of propionitrile. The solution was heated under reflux for 15 minutes chilled, and the crystals which separated were collected. Recrystallization was effected from MeCN to give 235 mg (44%) of complex compound 11 of Table 2. Infrared spectra of the products obtained by Methods A and B were identical.

Test Methods

Biological Methods.

The 2-acetylpyridine thiosemicarbazones and their selenosemicarbazone analogs were tested for antimalarial activity at the Dr. Leo Ran Laboratory, University of Miami, Fla., against a drug-sensitive strain of *Plasmodium berghei* (strain KBG 173) in mice. Five mice per dose level are infected by the intraperitoneal administration of parasitized erythrocytes. Untreated infected animals, which serve as controls, die, on the average, after 6.2 days. A candidate drug is given 72 hours after the mice are infected and is judged to be "toxic" if they die before the 6th day, "inactive" if they die between the 6th and 12th day, "active" if the mean survival time is at least doubled, and "curative" if the mice survive at least 60 days post infection. Compounds which are "active" or "curative" at a dose of 40 mg/kg are retested at several lower dose levels, but results are not reported unless extension of mouse survival time is observed. Details of the test procedure were reported by Osdene, Russel, and Rane in *J. Med. Chem.*, 1967, Vol. 10, page 431.

The antitumor activity of the thiosemicarbazones and their metal complexes was determined at the National Cancer Institute (N.I.H.), Bethesda, Md., by the standard screening procedure (cf. Instruction 14) in the P388 lymphocytic leukemia test system. The tumor inoculum of 10$^6$ ascites cells was implanted on day 0 ip in CD$_2$F$_2$(CDF$_1$) mice. The drugs were administered daily ip in accordance with the treatment schedule indicated in Table 4. A compound is considered active when T/C (test/control) survival times produce a percentage >125.

TABLE 2

Transition Metal Complexes of 2-Acetylpyridine Thiosemicarbazones

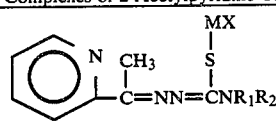

| Complex Compound No. | Ligand | M | X | mp, °C, dec | Formula | Yield, % | Recryst. solvent | Color and cryst. form |
|---|---|---|---|---|---|---|---|---|
| 1 | IV | Cu(II) | Cl$^-$ | 261–262 | C$_{14}$H$_{19}$ClCuS | 79 | DMF | dark green needles |
| 2 | IV | Ni(II) | Cl$^-$ | 278–279 | C$_{14}$H$_{19}$ClN$_4$NiS | 88 | DMF | reddish brown needles |
| 3 | IV | Fe(III) | 2Cl$^-$ | 217–218 | C$_{14}$H$_{19}$Cl$_2$FeN$_4$S | 80 | MeCN | black prisms |
| 4 | IV | Mn(II) | $a$ | 298–300 | (C$_{14}$H$_{19}$N$_4$S)$_2$Mn | 69 | DMF-H$_2$O | pale yellow needles |
| 5 | IV | Cu(II) | NCS$^-$ | 217–218 | C$_{15}$H$_{19}$CuN$_5$S$_2$ | 62 | PrCN | dark green prisms |
| 6 | IV | Ni(II) | NCS$^-$ | 234–236 | C$_{15}$H$_{19}$N$_5$NiS$_2$ | 59 | MeCN | reddish brown needles |
| 7 | IIIa | Cu(II) | Cl$^-$ | 260–261 | C$_{16}$H$_{21}$ClCuN$_4$S | 93 | DMF | dark green needles |
| 8 | IIIb | Cu(II) | Cl$^-$ | 273–274 | C$_{16}$H$_{21}$ClCuN$_4$Se | 90 | DMF | dark green needles |

TABLE 2-continued

Transition Metal Complexes of 2-Acetylpyridine Thiosemicarbazones

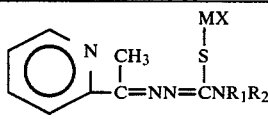

| Complex Compound No. | Ligand | M | X | mp, °C., dec | Formula | Yield, % | Recryst. solvent | Color and cryst. form |
|---|---|---|---|---|---|---|---|---|
| 9 | IIIa | Ni(II) | Cl⁻ | 300–302 | $C_{16}H_{21}ClN_4NiS$ | 85 | DMF | reddish brown needles |
| 10 | IIIa | Fe(III) | 2Cl⁻ | 271–272 | $C_{16}H_{21}Cl_2FeN_4S$ | 93 | MeCN | black hexagonal plates |
| 11 | IIIa | Cu(II) | NCS⁻ | 227–229 | $C_{17}H_{21}CuN_5S_2$ | 87 | MeCN | dark green prisms |
| 12 | IIIa | Ni(II) | NCS⁻ | 277–278 | $C_{17}H_{21}N_5NiS_2$ | 65 | MeCN | orange square plates |
| 13 | V | Cu(II) | Cl⁻ | 234–235 | $C_{15}H_{21}ClCuN_4S$ | 96 | DMF | bronze needles |
| 14 | V | Fe(III) | 2Cl⁻ | 216–218 | $C_{15}H_{21}Cl_2FeN_4S$ | 86 | MeOH | black cubes |

[a]Bis-ligand complex which crystallizes without a gegenion

TABLE 3

Antimalarial Activity of Transition Metal Complexes of 2-Acetylpyridine Thiosemicarbazones against *Plasmodium berghei* in Mice

| Compound No. | increase in mean survival time (days) and no. of cures at dosage, mg/kg[a] | | | | |
|---|---|---|---|---|---|
| | 40 | 80 | 160 | 320 | 640 |
| 1 | 3.9 | — | 9.1A | — | 0.1 |
| 2 | 0.2 | — | 0.6,T(1/5) | — | 1.8,T(4/5) |
| 3 | 4.3 | — | C(2/5) | — | T(4/5) |
| 4 | −0.4 | 3.2 | 4.6 | 7.1A | C(5/5) |
| 5 | C(1/5) | — | 6.5A | — | T(4/5) |
| 6 | — | — | −0.1 | — | 0.7 |
| 7 | 0.6 | C(2/5) | C(5/5) | C(1/5), T(4/5) | C(1/5), T(4/5) |
| 8 | 3.4 | 2.6 | 5.0 | 5.8 | 8.7A |
| 9 | 0.4 | — | 0.1 | — | −0.4 |
| | T(2/5) | | T(1/5) | | T(4/5) |
| 10 | 1.1 | — | 5.3 | — | C(4/5) |
| 11 | C(1/5) | 7.1A | C(2/5) | 7.8A | T(5/5) |
| 12 | 0.1 | — | 0.7 | — | −0.1 |
| 13 | C(1/5) | C(1/5) | C(1/5), T(3/5) | C(2/5), T(1/5) | C(2/5), T(3/5) |
| 14 | 0.1 | 3.5 | 7.3A | 13.0A | C(2/5) |

[a]T = toxic; A = active; C = cure

TABLE 4

Antitumor Activity of Transition Metal Complexes of 2-Acetylpyridine Thiosemicarbazones against Leukemia P388 in the Mouse

| Compound No. | Treatment Schedule | Dose, mg/kg | Weight Difference (T-C), % | T/C, % |
|---|---|---|---|---|
| 1 | A[a] | 25 | −3.6 | 121 |
| | | 12.5 | −3.4 | 126 |
| 3 | B[b] | 6.25 | −2.1 | 160 |
| | | 3.13 | −0.4 | 134 |
| | | 1.56 | 0.0 | 126 |
| 4 | A | 200 | −1.6 | 99 |
| | | 100 | −1.8 | 113 |
| 5 | B | 25 | −2.9 | 178 |
| | | 12.5 | −2.2 | 178 |
| | | 6.25 | −1.5 | 164 |
| 6 | B | 50 | −1.4 | 136 |
| | | 25 | −1.4 | 103 |
| | | 12.5 | −1.6 | 99 |
| 7 | A | 200 | −1.1 | 115 |
| | | 100 | −0.4 | 101 |
| 9 | B | 6.25 | −2.0 | 153 |
| 12 | B | 200 | −1.8 | 139 |
| | | 100 | −1.2 | 125 |
| | | 50 | −1.3 | 109 |
| 13 | A | 12.5 | −2.1 | 129 |
| | | 6.25 | −0.9 | 127 |
| | | 3.13 | −0.2 | 101 |

[a]Experimental animals were treated 4 times daily with the indicated dose, beginning on day 1 and ending on day 3.
[b]Experimental animals were treated 1 time daily with the indicated dose, beginning on day 1 and ending on day 5.

Utility

Antimalarial activity.

The ability to cure mice infected with *Plasmodium berghei* was investigated in a series of complexes of Fe(III), Cu(II), and Ni(II) with three $N^4,N^4$-disubstituted thiosemicarbazones of 2-acetylpyridine (Table 3). The free ligands showed curative activity (3/5 infected animals) at dosage levels from 40–160 mg/kg. Only one of the metal complexes approached this level of activity, namely, Cu(III) complex compound 7 of Table 2 which cured 5/5 infected animals at a dosage of 160 mg/kg. Complexes of Ni(II) were inactive, whereas complexes of Fe(III) were of lower activity than the corresponding Cu(II) complexes.

It is interesting to note that antimalarial activity was retained in this series of thiosemicarbazones upon complexaton with transition metals, these complexes appear to offer no therapeutic advantage over the free ligands.

Antitumor activity.

Nine thiosemicarbazone metal complexes were evaluated for antitumor activity against the P338 leukemia cell line in mice (Table 4). The free ligands posses intrinsic antitumor activity, exemplified by 3-azabicycli[3.2.2-]nonane-3-thiocarboxylic acid 2-[1-(2-pyridyl)ethylidene]hydrazide, IIIa, which has a T/C value of 126% at a dose level of 6.5 mg/kg. Selenium analog, IIIb, shows comparable activity with a T/C of 129% at the same dose level. Ligand IV was less active, having a T/C value of 117% at a dose of 6.25 mg/kg.

Most of the metal complexes which were investigated showed significant (T/C-125%) antitumor activity. As was the case in the antimalarial series, the highest level of activity was exhibited by a Cu(II) complex, i.e., complex compound 5 of Table 2. The Fe(III) complex 3, had only slightly lower activity. In constrast to the antimalarial findings, where Ni(II) complexes were inactive, Ni(II) complex compounds 6, 9, and 12 of Table 2 had significant antitumor activity. Whereas metal ion complexation lowers antimalarial activity, antitumor activity is enhanced by coordination.

We claim:

1. The compound of a formula

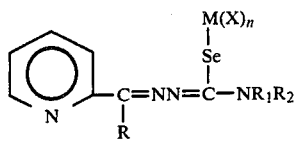

or a pharmaceutically-acceptable acid addition salt wherein X represents a negative radical selected from the group consisting of a halogen atom, or a thiocyanate group; M represents a transition metal selected from the group consisting of Cu(II), Ni(II), Fe(III), or Mn(II); n is 1 or 2; R is a lower alkyl selected from the group consisting of methyl and ethyl; $R_1$ is hydrogen, alkyl of 1 to 12 carbon atoms; cycloalkyl of 3 to 10 carbon atoms; substituted alkyl of 1 to 12 carbon atoms (wherein the substituent is amino, alkylamino of 1 to 4 carbon atoms, dialkylamino of 1 to 4 carbon atoms in each alkyl, cycloalkyl of 3 to 10 carbon atoms, hydroxy, C(0)0alkyl containing from 1 to 4 carbon atoms in each alkyl, phenyl, or pyridyl; alkenyl of 2 to 6 carbon atoms; alkynyl of 3 to 6 carbon atoms; substituted benzyl (wherein the substituent is methyl or phenyl on the alpha carbon atom, or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of 1 to 4 carbon atoms, fluoro, alkoxy of 1 to 4 carbon atoms, hydroxy, phenoxy, trifluoromethyl, dimethylamino, diethylaminomethyl, or C(0)0alkyl of 1 to 4 carbon atoms in the alkyl group); pyridyl; thienyl; indolyl, furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:
  (1) alkylenimino which is either bridged by an alkylene group of 3 to 12 carbon atoms, or is fused to a phenyl ring, or is attached by a spiro linkage to an ethylene ketal group;
  (2) homopiperazinyl; homopiperazinyl substituted with alkyl of 1 to 4 carbon atoms; piperazinyl; or piperazinyl substituted with alkyl of 1 to 4 carbon atoms, dialkyl of 1 to 4 carbon atoms in each alkyl, phenyl, C(0)0alkyl of 1 to 4 carbon atoms in the alkyl group, trifluoromethylphenyl, halophenyl, benzyl, or pyridyl;
  (3) alkylenimino having 3 to 12 carbon atoms;
  (4) alkylenimino 3 to 12 which may contain one double bond and/or is mono- or disubstituted with alkyl of 1 to 4 carbon atoms in each alkyl, hydroxy, phenyl, or benzyl; and
  (5) morpholino; or dialkylmorpholino having 1 to 4 carbon atoms in each alkyl.

2. A compound of claim 1 wherein X represents a negative radical selected from the group consisting of chloride, or a thiocyanate group; M represents a transition metal selected from the group consisting of Cu(II), Ni(II), Fe(III), or Mn(II); n is 1 or 2; R is a lower alkyl selected from the group consisting of methyl and ethyl; $R_1$ is hydrogen, alkyl of 1 to 12 carbon atoms; cycloalkyl of 3 to 10 carbon atoms; substituted alkyl of 1 to 12 carbon atoms (wherein the substituent is amino, alkylamino of 1 to 4 carbon atoms, dialkylamino wherein the alkyl groups each contain 1 to 4 carbon atoms; cycloalkyl or 3 to 10 carbon atoms, hydroxy, C(0)0alkyl wherein the alkyl group contains 1 to 4 carbon atoms, phenyl, or pyridyl); alkenyl of 2 to 6 carbon atoms; alkynyl of 3 to 6 carbon atoms; substituted benzyl (wherein the substituent is methyl or phenyl on the alpha carbon atom, or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of 1 to 4 carbon atoms, halo, alkoxy of 1 to 4 carbon atoms, hydroxy, phenxoy, trifluoromethyl, dimethylamino, diethylaminomethyl or C(0)0alkyl wherein the alkyl group has 1 to 4 carbon atoms); pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of: azetidino; pyrrolidino; 2,5-dimethylpyrrolidino; piperidino;

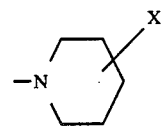

(wherein X is 2-methyl, 3-methyl, 4-methyl, 2-ethyl, 4-hydroxy, 4-phenyl, or 4-benzyl); hexamethylenimino; octamethylenimino; dodecamethylenimino; 2,6-dimethyl piperidino; 3,5-dimethylpiperidino; morpholino; 3,5-dimethylmorpholino;

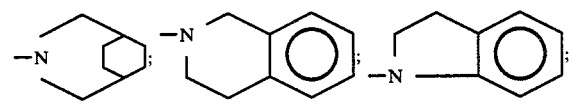

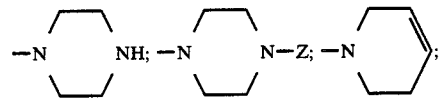

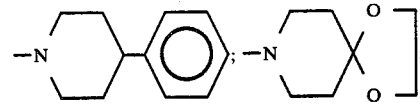

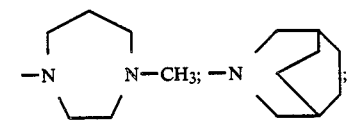

azacyclotridecyl, wherein Z is methyl, phenyl, 3-trifluoromethylphenyl, benzyl, C(0)Et, 3-pyridyl, 2-pyridyl, or 4-fluorophenyl.

3. A compound of salt of claim 1 wherein the moiety depicted by the formula

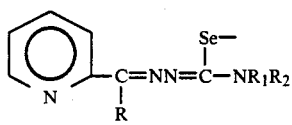

is derived from the group of compounds selected from the group consisting of 1-Azacycloheptane-1-selenocarboxylic acid 2-[1-(2-pyridyl)ethylidene]hydrazide; 2-Acetylpyridine 4-(3-fluorophenyl)-3-selenosemicarbazone; 3-Azabicyclo[3.4.4]nonane-3-selenocarboxylic acid 2-[1-(2-pyridyl)ethylidene]hydrazide; 1-Methylamino-1-deoxy-D-glucitol-N-selenocarboxylic acid 2-[1-(2-pyridyl)ethylidene]hydrazide; 2-Acetylpyridine 4,4-dimethylselenosemicarbazone; 2-Acetylpyridine 4-(1-adamantyl)selenosemicarbazone; 2-Acetylpyridine 4-cyclohexyl-4-methylselenosemicarbazone; 2-Acetylpyridine 4-methylselenosemicarbazone; 2-Acetylpyridine selenosemicarbazone; Azetidine-1-selenocarboxylic acid 2-[1-(2-pyridyl)ethylidene]hydrazide; 1-Azacyclopentane-1-selenocarboxylic acid 2-[1-(2-pyridyl)ethylidene]hydrazide; Piperidine-1-selenocarboxylic acid 2-[1-(2-pyridyl)ethylidene]hydrazide; 2-Methylpiperidine-1-selenocarboxylic acid 2-[1-(2-pyridyl)ethylidene]hydrazide; 2-Ethylpiperidine-1-selenocarboxylic acid 2-[1-(2-pyridyl)ethylidene]hydrazide; 1-Azacyclotridecane-1-selenocarboxylic acid 2-[1-(2-pyridyl)ethylidene]hydrazide; 2-Acetylpyridine 4-allyl-3-selenosemicarbazone; 2-Acetylpyridine 4-(2-picolyl)-3-selenosemicarbazone; 2-Acetylpyridine 4-cyclohexyl-3-selenosemicarbazone; 2-Acetylpyridine 4-phenyl-3-selenosemicarbazone; 2-Acetylpyridine 4-(1,1,3,3-tetramethylbutyl)-3-selenosemicarbazone; 1,4-Diaza-4-carboethoxycyclohexane-1-selenocarboxylic acid 2-[1-(2-pyridyl)ethylidene]hydrazide; 1,4-Diaza-4-phenylcyclohexane-1-selenocarboxylic acid 2-[1-(2-pyridyl)ethylidene]hydrazide; 2-Acetylpyridine 4-(2-methylbenzyl)-3-selenosemicarbazone; 2-Acetylpyridine 4-(4-trifluoromethyl-phenyl)-3-selenosemicarbazone; 1,4-Diaza-4-(2-pyridyl)cyclohexane-1-selenocarboxylic acid 2-[1-(2-pyridyl)ethylidene]hydrazide; 1,4-Diaza-4-(2-pyridyl)cyclohexane-1-selenocarboxylic acid 2-[1-(2-pyridyl)ethylidene]hydrazide dihydrochloride; 2-Acetylpyridine 4-benzyl-3-selenosemicarbazone; 1,4-Diaza-4-methylcycloheptane-1-selenocarboxylic acid 2-[1-(2-pyridyl)ethylidene]hydrazide; 2-Acetylpyridine 4-(2-propynyl)-3-selenosemicarbazone; 2-Acetylpyridine 4,4-diethylselenosemicarbazone; 2-Acetylpyridine 4-ethylselenosemicarbazone; 2-Acetylpyridine 4-butylselenosemicarbazone; 2-Acetylpyridine 4-octylselenosemicarbazone; 2-Acetylpyridine 4-decylselenosemicarbazone; 2-Acetylpyridine 4-(2-phenethyl)selenosemicarbazone; (4-Hydroxy-4-phenylpiperidine)-1-selenocarboxylic acid 2-[1-(2-pyridyl)ethylidene]hydrazide; 2-Acetylpyridine 4-(3-pinylmethyl)selenosemicarbazone; and 1-Azacyclononane-1-selenocarboxylic acid 2-[1-(2-pyridyl)ethylidene]hydrazide.

4. A compound or salt of claim 2 wherein R is methyl and NR₁R₂ is selected from the group consisting of:

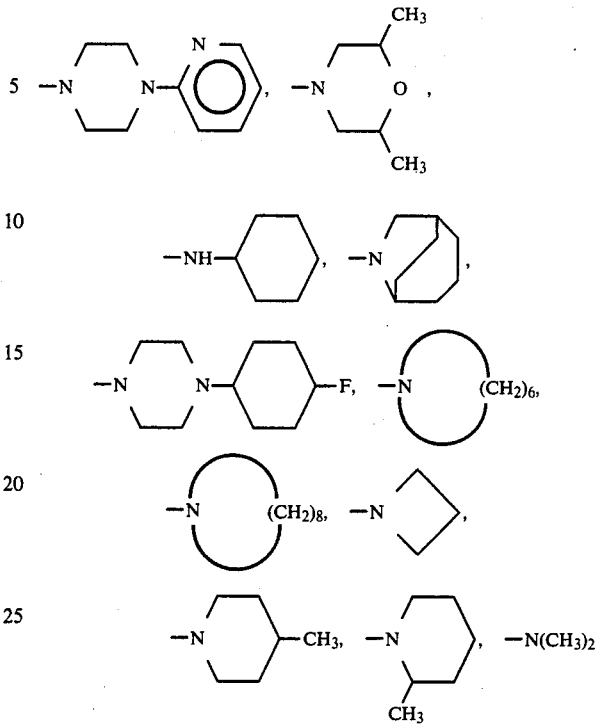

and —N(CH₂CH₃)₂.

5. A compound or salt of claim 4 wherein NR₁R₂ is selected from the group consisting of:

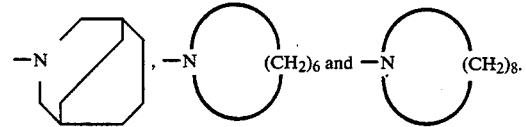

6. A compound or salt of claim 5 wherein M is Ni(II), X is Cl and n is 1.

7. A compound or salt of claim 5 wherein M is Fe(III), X is Cl and n is 2.

8. A compound or salt of claim 5 wherein M is Cu(II), X is —NCS and n is 1.

9. A compound or salt of claim 5 wherein NR₁R₂ is

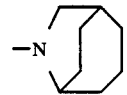

10. A compound or salt of claim 9 wherein M is Cu(II), X is Cl and n is 1.

11. A compound or salt of claim 5 wherein NR₁R₂ is

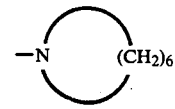

12. A compound or salt of claim 11 wherein M is Cu(II), X is Cl, and n is 1.

13. A compound or salt of claim 11 wherein M is Ni(II), X is Cl, and n is 1.

14. A compound or salt of claim 11 wherein M is Fe(III), X is Cl, and n is 2.

15. A compound or salt of claim 11 wherein M is Mn(II).

16. A compound or salt of claim 11 wherein M is Cu(II), X is —NCS, and n is 1.

17. A compound or salt of claim 5 wherein $NR_1R_2$ is

18. A compound or salt of claim 17 wherein M is Cu(II), X is Cl and n is 1.

19. A compound or salt of claim 17 wherein M is Fe(III), X is Cl and n is 2.

20. The process of preparing the compounds of claim 1 which comprises:

(a) reacting a thiosemicarbazone of the formula

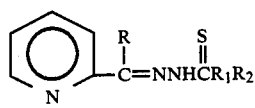

with methyliodide in the presence of aqueous or alcoholic base; and (b) reacting the product of step (a) with sodium hydrogen selenide under inert atmosphere; and (c) reacting the seleno semicarbazone product of step (b) with a transition metal halide or thiocyanate.

21. The process of preparing the $N^4$-phenyl compounds of claim 1 which comprises:

(a) reacting selenium with sodium borohydride;

(b) reacting the sodium hydrogen selenide product of step (a) with sodium hydroxide;

(c) reacting the sodium selenide product of step (b) with a compound having the formula

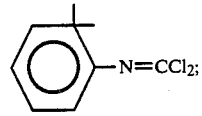

(d) reacting the phenylisoselenocyanate product of step (c) with 2-acetylpyridine hydrazone to yield 2-acetylpyridine 4-phenyl-3-selenosemicarbazone; and (e) reacting the selenosemicarbazone product of step (b) with a transition metal halide or thiocyanate.

22. A method of treating an animal which has a malarial infection by administering to said animal a therapeutically-effective amount of a compound or pharmaceutically-acceptable acid addition salt of claim 1.

23. A method of treating an animal which has leukemia by administering to said animal a therapeutically-acceptable acid addition salt of claim 1.

* * * * *